United States Patent [19]

Vukos et al.

[11] Patent Number: 5,389,181

[45] Date of Patent: Feb. 14, 1995

[54] FEMININE HYGIENE ARTICLE AND METHOD

[75] Inventors: John P. Vukos; Billie D. Matelski, both of Neenah, Wis.

[73] Assignee: Kimberly-Clark Corporation, Neenah, Wis.

[21] Appl. No.: 140,366

[22] Filed: Oct. 20, 1993

Related U.S. Application Data

[62] Division of Ser. No. 962,513, Oct. 15, 1992, Pat. No. 5,290,262.

[51] Int. Cl.$^6$ .............................................. B32B 31/00
[52] U.S. Cl. .................................... 156/264; 156/256; 156/266; 156/73.4; 156/308.2; 156/308.4; 156/198; 156/217; 156/221; 604/331
[58] Field of Search ............... 604/327, 328, 330, 331, 604/358, 904, 385.1; 156/256, 264, 266, 73.4

[56] References Cited

U.S. PATENT DOCUMENTS

| | | | |
|---|---|---|---|
| 2,092,346 | 6/1936 | Arone | 128/284 |
| 2,331,355 | 10/1943 | Strongson | 128/290 |
| 3,420,234 | 1/1969 | Phelps | 128/285 |
| 3,690,321 | 9/1972 | Hirschman | 128/285 |
| 3,905,372 | 9/1975 | Denkinger | 128/285 |
| 4,286,596 | 9/1981 | Rubinstein | 604/904 X |
| 4,531,945 | 7/1985 | Allison | 604/378 |
| 4,595,392 | 6/1986 | Johnson et al. | 604/358 X |
| 4,648,867 | 3/1987 | Conner et al. | 604/14 |
| 4,795,422 | 1/1989 | Conner et al. | 604/14 |
| 5,057,096 | 10/1991 | Faglione | 604/358 X |
| 5,135,475 | 8/1992 | Nakanishi et al. | 604/904 X |
| 5,169,394 | 12/1992 | Jean | 604/385.1 |

FOREIGN PATENT DOCUMENTS

| | | | |
|---|---|---|---|
| 804950 | 3/1974 | Belgium . | |
| 0316771 | 5/1989 | European Pat. Off. | A61F 13/18 |
| 0343941 | 11/1989 | European Pat. Off. | A61F 13/18 |
| 0426197 | 5/1991 | European Pat. Off. | A61F 13/46 |
| 2550438 | 5/1977 | Germany | A61F 13/18 |
| 1412111 | 10/1975 | United Kingdom . | |
| 1537272 | 1/1990 | U.S.S.R. | 604/330 |
| 8911843 | 12/1989 | WIPO | A61F 13/16 |

Primary Examiner—David A. Simmons
Assistant Examiner—M. Curtis Mayes
Attorney, Agent, or Firm—Mark L. Davis

[57] ABSTRACT

An absorbent feminine hygiene article has an external absorbent pad for disposition against the labia majora of a user, and a nonabsorbent flexible sheath for extending into the vagina. The sheath intercepts body fluid in the vagina and directs it to the external pad. A conducting layer conducts fluid so intercepted by the sheath to an absorbing surface on the interior of the external pad, the interior absorbing surface being displaced from the user's body by a primary mass of an absorbent layer.

17 Claims, 3 Drawing Sheets

FEMININE HYGIENE ARTICLE AND METHOD

This is a divisional application of copending application Ser. No. 07/962,513 filed Oct. 15, 1992, now U.S. Pat. No. 5,290,262.

FIELD OF THE INVENTION

This invention relates to sanitary articles which are used to receive and absorb body fluids such as menses, blood, urine, and other fluids released from a woman's body.

BACKGROUND OF THE INVENTION

As used herein, in both the specification and claims, "body fluid" includes all fluids released from a woman's body proximate the labia majora, including menses, blood, and urine. Articles known for receiving and absorbing body fluid tend to correspond to one of three types of construction. The first type of construction comprises an internally-used absorbent tampon which is inserted into the vagina. The absorbent tampon-type device generally intercepts and absorbs the menses fluid in the vagina. Thus, the intercepted fluid is retained in the vagina, albeit held in the tampon contained therein, whereby menses fluid generally does not reach the external body tissues propinquant the vagina. Exemplary of such internally-used tampon is U.S. Pat. No. 4,795,422 issued to Conner et al.

Desirably, tampons tend to intercept the menses fluid inside the body, whereby, in theory, the menses fluid does not flow freely out of the body on body tissues. However, during the times of heavy fluid flow, fluid can leak past the tampon, whereby an external pad may need to be used in combination with the tampon. Further, some users experience discomfort related to the use of a tampon, especially when the normal bulk of the tampon has been increased by absorption of menses fluid. So conventional tampons may sometimes have disadvantages related to leakage, and may sometimes cause discomfort derived from their bulk inside the vagina.

The second type of construction comprises an externally-worn absorbent pad adapted to be disposed on the outside of the body against the labia majora. Such a pad generally intercepts and absorbs the menses fluid at or adjacent the introitus of the vagina, or outside the vagina after the fluid has left the vagina completely. Exemplary of such an externally-worn absorbent pad is U.S. Pat. No. 2,331,355 issued to Strongson.

Externally-worn pads generally do not intrude into the highly sensitive introitus and the general interior of the vagina, and so may be more comfortable to the wearer, at least when first put in place. However, when using such external pads, menses fluid flows on the body tissues at and near the introitus before reaching the pad and being absorbed into the pad. This contact between menses fluid and the external body tissues propinquant the vagina can cause discomfort. In addition, since the fluid is absorbed into the absorbent material in the pad through the surface of the pad facing the body, the surface of the pad facing the body tends to be somewhat wet with menses fluid, and accordingly uncomfortable. Thus, conventional external pads fail to inhibit contact between menses fluid and the body tissues propinquant the vagina, and those body tissues tend to stay uncomfortably moistened by menses fluid. Finally, the external pad is generally held in place by securing it to the user's undergarment. When the undergarment shifts, the pad shifts also, whereby the pad is sometimes shifted out of its desired position propinquant the introitus. This shift of the pad commonly results in leakage of menses fluid around the pad and onto the user's garments.

Accordingly, there has been considerable investigation into a third type of construction, namely articles directed at intercepting body fluid both inside, and outside, of the vagina. Such articles prevent the body fluid from reaching the body tissues propinquant the vagina, while addressing potential leakage onto the external body tissues propinquant the vagina. Such articles comprise a combination of elements, one of which has the characteristics of an internal tampon, and another of which has the characteristics of an external pad. Exemplary of such combination articles are those disclosed in the following U.S. Pat. Nos.: 2,092,346 issued to Arone; 3,420,234 issued to Phelps; 3,690,321 issued to Hirschman; 3,905,372 issued to Denkinger. United Kingdom patent 1,412,111 issued to Alemany teaches all three related types of construction, namely an internal tampon, an external pad, and in combination an internal tampon and an external shield having a fluid-absorbing peripheral strip.

While all the above combination articles offer an external pad for absorbing at least some of the fluid received, thus tending to overcome the leakage issue associated with tampons, all of the means offered for intercepting the fluid in the vagina comprise absorbent tampon-like devices adapted to absorb fluid and hold it in the vagina. But it is precisely such tampon-like structures in the vagina which can make tampons feel uncomfortable. Furthermore, none of these designs address the issue of leakage around external pads.

So, while conventionally-known articles tend to reduce the potential for leakage related to use of tampons, they do not address the issue of leakage around external pads. Nor do they solve the problem of discomfort, either discomfort from intrusion of the bulky tampon into the vagina, or discomfort from body fluid spreading onto the body tissues outside the vagina before being absorbed into the pad.

SUMMARY OF THE DISCLOSURE

Briefly, the present invention relates to an absorbent feminine hygiene article. The article has an external pad with an absorbent layer adapted to receive and absorb body fluid. The absorbent layer has first and second opposing major surfaces and edges extending therebetween. The edges correspond to the outer perimeter of the absorbent layer. The external pad includes a liquid-impermeable baffle which overlies the entire second major surface. A nonabsorbent, flexible sheath outwardly extends from the external pad and is adapted to extend a distance sufficient to permit insertion of at least a portion of the sheath into the vagina of a user when the external pad is placed against the user's labia majora.

Preferably, the external pad comprises an opening extending vertically through the absorbent layer. The opening is disposed inwardly of the outer perimeter of the absorbent layer and has edges defining the inner perimeter about the opening. The sheath extends from the baffle through the opening.

The purpose of the nonabsorbent, flexible sheath is to intercept body fluid, such as menses, inside the user's body. The intercepted body fluid is preferably guided to the absorbent layer in the external pad by a conducting layer disposed between the absorbent layer and the baffle, and extending onto the sheath. The conducting layer is adapted to route the body fluid from the sheath to the second major surface of the absorbent layer whereby the majority of the fluid received by the absorbent layer, and thus the majority of the fluid absorbed into the pad, is received through the second major surface, which is displaced from the user's body by the primary mass of the absorbent layer.

Typically, the pad includes a cover overlying the first major surface of the absorbent layer. The cover has an opening, effectively sized smaller than and generally aligned with the opening in the absorbent layer. The conducting layer also has an opening effectively sized smaller than and generally aligned with the opening in the absorbent layer. Thus, the edges of the opening in the absorbent layer are spaced from the sheath by the cover and by the conducting layer.

In a preferred embodiment, the sheath is adapted to extend outwardly beyond the external pad by a distance sufficient that, when the sheath is fully extended in the user's vagina, the sheath will secure the positioning of the external pad, holding the pad substantially stationary, longitudinally and transversely, with respect to the vagina.

This invention also comprehends a method of fabricating the above-identified absorbent article. The method includes the step of selecting a soft, liquid-impermeable film suitable for contact with the female genitalia. The film is cut into a pair of blanks, each shaped such that, when joined together, the combination thereof can comprehend the entirety of the area of the pad, including the predetermined outer perimeter and shape of the pad. Each blank includes a perimeter edge portion which will ultimately form part of the outer perimeter of the pad. The perimeter edge portion extends from a first point along a first perimeter path to a second point, and thereby describes substantially half of the perimeter of the pad. Each blank also has a joinder edge portion adapted to be joined with the other blank of the pair. The joinder edge portion extends between the first and second points along a second path, different from the first path. The second path, at an intermediate locus, extends away from the perimeter portion to describe sheath portions. The blanks are joined at their respective joinder edge portions. The joined blanks are bent to create first and second generally parallel joined major surfaces. A film sheath comprising an extension of the baffle is adapted to be disposed vertical to the first and second major surfaces, thereby creating a baffle corresponding to the predetermined outer perimeter of the pad, in combination with the sheath. The film sheath and the baffle are both impervious to body fluid. Preferably, the absorbent layer has an opening adapted to receive the film sheath therethrough, and the method includes the step of extending the film sheath through the opening in the absorbent layer.

The method preferably includes the step of positioning a conducting layer between the absorbent layer and the baffle. The conducting layer is positioned adjacent to and faces the absorbent layer and is adapted to route body fluid within the conducting layer in preference to releasing it to the absorbent layer.

The method can also include the step of placing a cover over the absorbent layer such that the absorbent layer is between the cover and the baffle. Openings aligned with, and sized smaller than, the opening formed in the absorbent layer can be formed in the cover and the conducting layer. This enables the edges of the opening in the absorbent layer to be spaced from the sheath by portions of the cover and the conducting layer.

The general objects of this invention are to provide an absorbent feminine hygiene article having an intercepting element which intercepts body fluid inside the vagina, and to conduct the intercepted fluid to a remote interior surface of the absorbent feminine hygiene article, for absorption into the absorbent layer thereof from the remote interior surface. A more specific object of this invention is to provide a sanitary article having an intercepting element which is disposed in the user's vagina and an external pad whereby body fluid contacting the intercepting element is transferred to the external pad without substantial retention of fluid in the intercepting element.

Another object of this invention is to provide an absorbent article which conducts body fluid to an absorbent layer at a surface in the pad which is displaced from the user's body by a primary mass of the absorbent layer, such that the majority of the body fluid absorbed into the absorbent material is absorbed at the displaced surface.

Still another object of this invention is to provide an absorbent feminine pad having a nonabsorbent, intercepting element comprising a flexible sheath extending vertically through an opening in the absorbent layer of the pad, whereby the sheath may be introduced into the vagina when the pad is placed against the labia majora.

Still another object of this invention is to provide a conducting layer with the sheath, such that the conducting layer conducts body fluid to a surface of an absorbent material, which surface is displaced from the user's body by a primary mass of an absorbent layer.

Further, another object of this invention is to provide a method of fabricating an absorbent pad having a nonabsorbent sheath extending from a nonabsorbent baffle, by joining together pairs of material blanks wherein each blank comprises generally half of the material required to form the composite baffle and sheath.

Another object of this invention is to provide a method of securing an external pad to a user's body without discomfort to the user, such that shifting of the undergarment does not correspondingly shift the external pad away from the user's vaginal opening, thereby inherently reducing leakage around the pad.

Other objects and advantages of the present invention will become more apparent to those skilled in the art in view of the following description and the accompanying drawings.

DETAILED DESCRIPTION OF THE PREFERRED EMBODIMENTS

Figure 1:
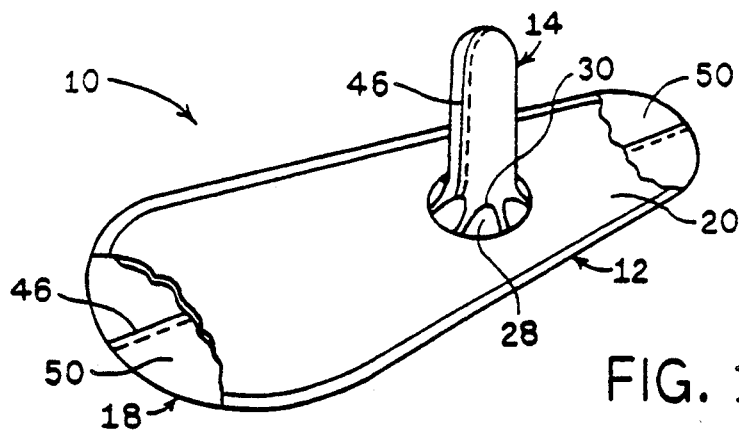
FIG. 1 is a pictorial view of an absorbent feminine hygiene article of the invention, with parts cut away.
Figure 2:
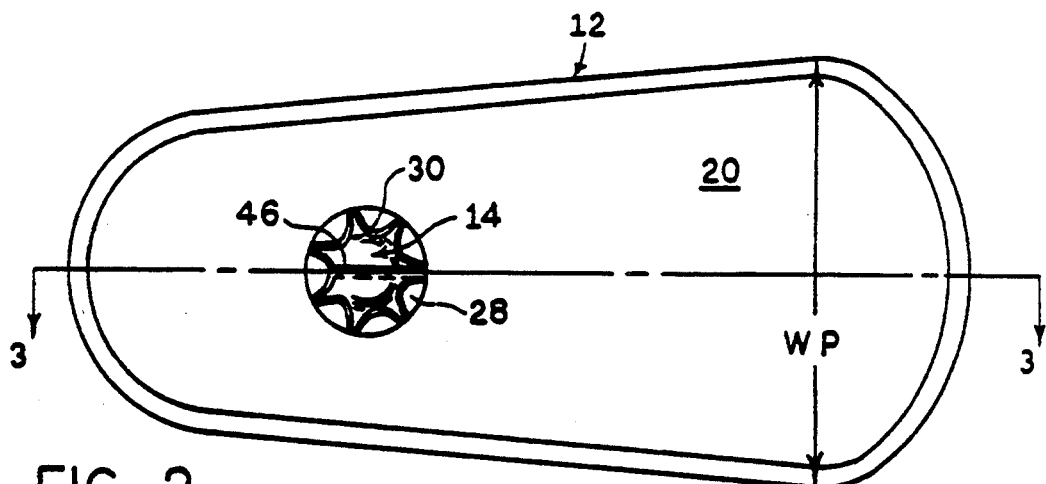
FIG. 2 is a top view of the absorbent feminine hygiene article of FIG. 1.
Figure 3:
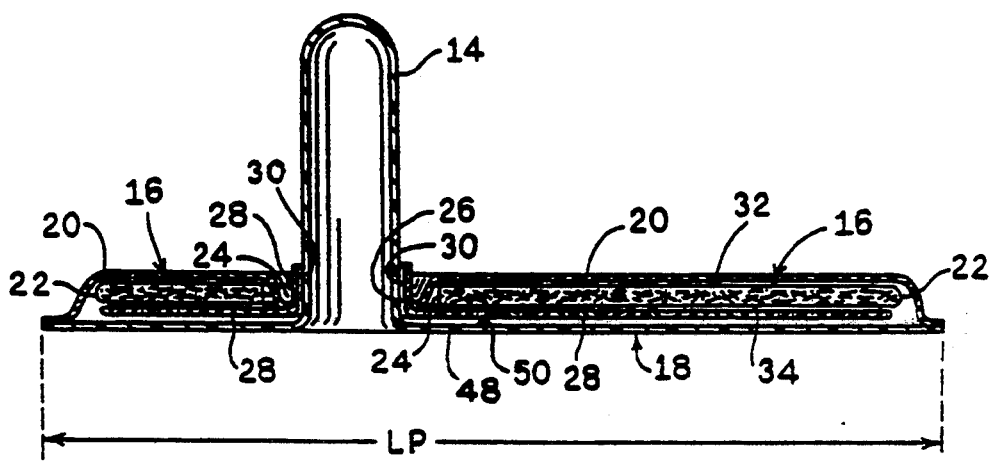
FIG. 3 is a cross-section of the hygiene article taken along line 3—3 of FIG. 2.

Referring to FIGS. 1-3 an absorbent feminine hygiene article 10 is illustrated. The absorbent feminine hygiene article 10 has an external pad 12, for placement against the labia majora, and a outwardly extendable, nonabsorbent flexible sheath 14, which is adapted to be extended into the user's vagina. FIGS. 1-7 illustrate an assymetric pad which is narrower at one end and having the sheath located closer to the narrow end. In should be noted that a symmetrical pad is more customary and the sheath could be centrally located on the pad.

The external pad 12 has an absorbent layer 16, see FIG. 3, disposed and trapped between a liquid-impervious baffle 18 and a liquid-pervious cover 20. The absorbent layer 16 has a peripheral edge 22 extending thereabout. The absorbent layer 16 also has an opening 24 extending therethrough which is disposed inwardly of the outer perimeter 22. The cover 20 has a corresponding opening 26 generally aligned with and sized smaller than the opening 24. A conducting layer 28 is disposed between the absorbent layer 16 and the baffle 18 and has an opening 30. The opening 30 is generally aligned with and sized smaller than the opening 24. The conducting layer 28, by means of the edges of its opening 30, extends onto the sheath 14, whereby portions of the conducting layer 28 are disposed between the sheath 14 and cover 20. The edges of the opening 26 formed in the cover 20 are disposed between the sheath 14 and the edges of the opening 24 formed in the absorbent layer 16. The edges of the opening 26 are also present between the edges of the opening 24 formed in the absorbent layer 16 and that portion of the conducting layer 28 which is disposed against the sheath 14. Accordingly, the edges of the opening 24 formed in the absorbent layer 16 are spaced from the sheath 14 by portions of the conducting layer 28 and the cover 20, and are spaced from that portion of the conducting layer 28 which is disposed against the sheath 14 by the cover 20. Thus, body fluid cannot transfer directly from the sheath 14 to the edges of the opening 24 nor can the fluid transfer directly from the conducting layer 28 at the sheath 14 to the edges of the opening 24.

The absorbent layer 16 is the primary structure within the external pad 12 which absorbs and holds the expelled body fluids, for example: menses, blood, urine, etc. The absorbent layer 16 can be fabricated from any suitable absorbent material which can receive and hold water-based fluids, such as menses. Conventional superabsorbent materials can be utilized in the absorbent layer 16. A typical superabsorbent material is Gelok Fam 840 Sam Laminate, which is commercially available from Gelok International Corporation, Dunbridge, Ohio 43414. The amount and thickness of the material used in the absorbent layer 16 can vary with the absorption capacity desired for a given pad. The capacity is generally related to the amount of absorptive material used. Those skilled in the art are well able to determine the amount and type of absorbent material to be used for the absorbent layer for a given pad.

Referring to FIG. 3, the absorbent layer 16 has a first major surface 32 disposed toward the cover 20 and a second major surface 34 disposed toward the baffle 18.

The liquid-impermeable baffle 18 provides the primary barrier to leakage of the body fluid out of the external pad 12. For ease of fabrication of the absorbent feminine hygiene article 10, the baffle 18 and the sheath 14 are fabricated as one integral unit whereby the same material is used for both. The characteristics of the material used for the baffle 18 and the sheath 14 include: its compatibility with use against the female genitalia; its imperviousness to menses; its softness; and its flexibility. Soft polyethylene films are generally suitable for use in fabricating the baffle 18 and the sheath 14. A suitable material is polyethylene film having a thickness of about 1.2 mils. This film is commercially available from Dupont Corporation as MPX polyethylene film.

The liquid-permeable cover 20 can be fabricated from material typically used to fabricate the covers in feminine pads. For example, the cover 20 can be fabricated from spunbonded polypropylene having a weight of about 0.8 grams per square meter.

The conducting layer 28 performs the function of receiving body fluid from the sheath 14, preferably outside of the introitus, and conducting the body fluid to the second major surface 34 of absorbent layer 16. Here, the body fluid is absorbed into and retained by the absorbent layer 16. Accordingly, the conducting layer 28 must have sufficient capillary activity, or other means to attract and transport the body fluid from the sheath 14 to the second major surface 34. Preferably, the conductive layer 28 has a density greater than the second major surface 34. A suitable material for the conducting layer 28 is a meltblown polypropylene layer, having a thickness of about 0.6 mm., a weight of about 60 grams per square meter, mean fiber diameter of about 3.9 micrometers, and pore size of about 10.6 micrometers.

The conducting layer 28 is generally coextensive with the second major surface 34. The relative amounts of capillary attraction in the absorbent layer 16 at surface 34, and the conducting layer 28 are such that the body fluid is preferably held in the conducting layer 28. However, when high levels of fluid loading occurs in the conducting layer 28, the fluid is transferred to the absorbent layer 16. As a result, the conducting layer 28 retains high loading of body fluid over its entire surface area and distributes the body fluid generally along the entirety of the adjacent second major surface 34. This results in the body fluid being absorbed into the absorbent layer 16 about generally the entire area of the second major surface 34. Accordingly, essentially the full area of the second major surface 34 is efficiently utilized in the process of absorbing body fluid.

Figure 4:
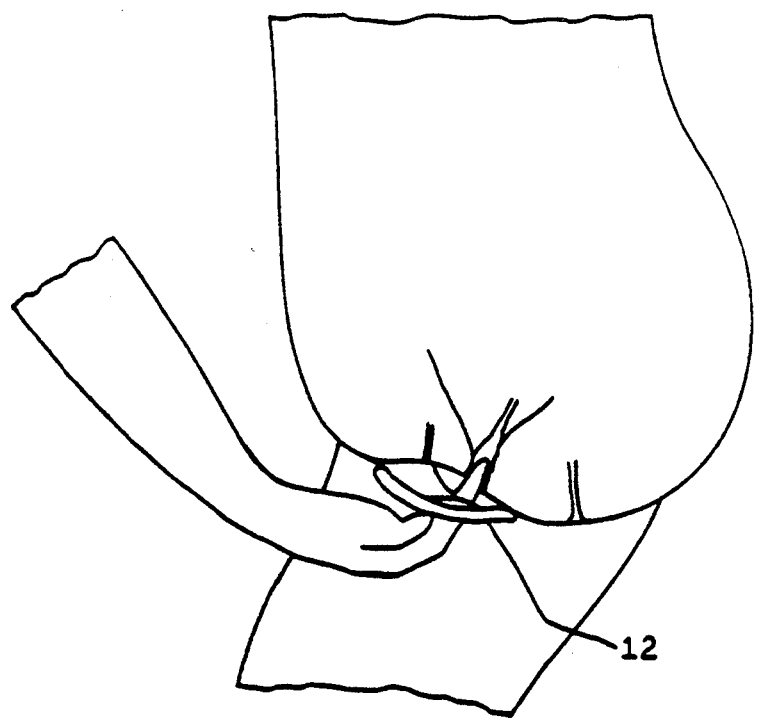
FIG. 4 is a schematic view showing the hygiene article depicted in FIG. 1, being positioned by the user.
Figure 5:
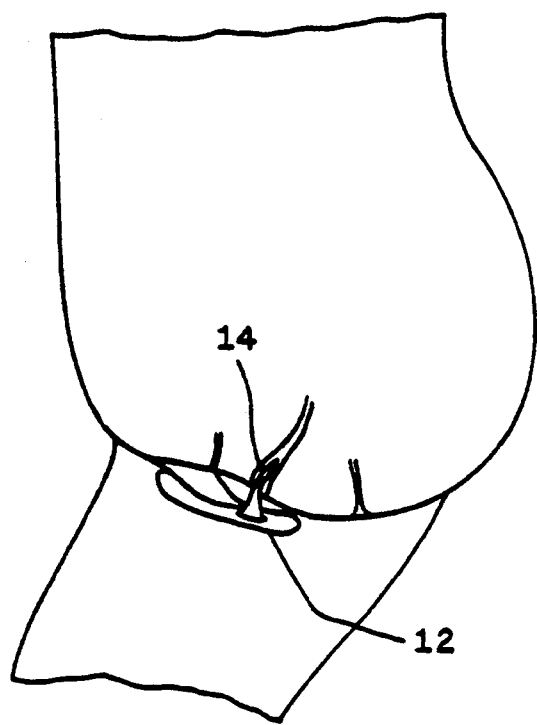
FIG. 5 is a schematic view showing the hygiene article depicted in FIG. 1, in position on the body with the external pad disposed against the labia majora of the user and a portion of the intercepting sheath in the vagina.

Referring to FIGS. 4 and 5, the nonabsorbent sheath 14 is designed such that a significant portion of the sheath 14 can be disposed in the user's vagina when the external pad 12 is placed against the labia majora. Accordingly, the sheath should be long enough that the distal end of the sheath can be placed well inside the introitus. However, because the vagina is so sensitive, the sheath should not be so long as to suggest placing more sheath material than necessary in the vagina. A sheath will thus extend vertically from the external pad 12 by a distance of about 10 mm. to about 70 mm.

Because the sheath 14 is soft and flexible, it can collapse after placement in the vagina, whereby the sheath 14 occupies a minimum volume. As a result of the softness and flexibility of the sheath 14, and its minimal volume, the sheath 14 does not cause the discomfort typically associated with the bulk of conventional tampons since, even though the sheath 14 has a presence in the vagina, the bulk and volume so occupied, is minimal. The sheath 14 is nonabsorbent and, therefore, it does not accumulate body fluid nor will it hold the body fluid in the vagina as a tampon does. The sheath 14 performs two primary functions. First, the sheath 14 serves a holding function, to hold the external pad 12 substantially stationary, preventing substantial movement, longitudinally and transversely, with respect to the vagina, so that the external pad 12 cannot slip off the labia majora and/or away from the introitus. The sheath 14 does, however, permit limited rotational movement of the external pad 12 about the vagina, so the external pad 12 can twist and turn with corresponding twists and turns of the external body surfaces. Accordingly, holding the external pad 12 in place against the user's body does not rely on securing the external pad 12 to the user's undergarment. Thus, when using the absorbent feminine hygiene article 10, movements of the undergarment have less affect on the positioning of the external pad 12 than where a sanitary pad is secured to the undergarment. The present invention enables the external pad 12 to experience less movement with respect to the labia majora and correspondingly to spend a greater amount of the time properly positioned against the labia majora. This results in proper reception of fluid into the external pad 12 over a greater amount of time. This corresponds to less leakage of body fluid around the edge of the article 10.

The second primary function of the sheath 14 is that it intercepts body fluid inside the vagina. Body fluid which comes into contact with the sheath 14 is intercepted and diverted by the sheath 14 such that it tends to flow downward along the surface of sheath 14, in preference to flowing along the surfaces of the body tissue outside the introitus toward the external pad 12. When the body fluid reaches the conducting layer 28 it will transfer into it. The conducting layer 28 routes or conducts the body fluid, generally by principles of capillarity, to the second major surface 34. The second major surface 34 is located on the lower side of absorbent layer 16 which is disposed away from the user's labia majora. The body fluid is then absorbed through the second major surface into the absorbent layer 16.

As just explained, after the body fluid is intercepted by the sheath 14, it follows the sheath 14 downward into the external pad 12. Here, the body fluid is absorbed into the absorbent layer 16 and retained. Thus, the absorbent layer 16 is generally loaded through the bottom or second major surface 34. This bottom loading diverts a majority of the body fluid from flowing along external body tissues, thereby significantly reducing the amount of body fluid which needs to be absorbed from those body tissues, through the cover 20 and the first major surface 32.

There are two significant advantages from reducing the amount of body fluid absorbed through the cover 20 and first major surface 32. First, the cover 20 remains drier, improving the user's comfort as related to surface moisture. Second, since less body fluid is loaded into the absorbent layer 16 through the first major surface 32, less body fluid is present on the cover 20, and there is less risk of fluid leakage around the external pad 12 before it is absorbed by the absorbent layer 16.

METHOD

Figure 6:
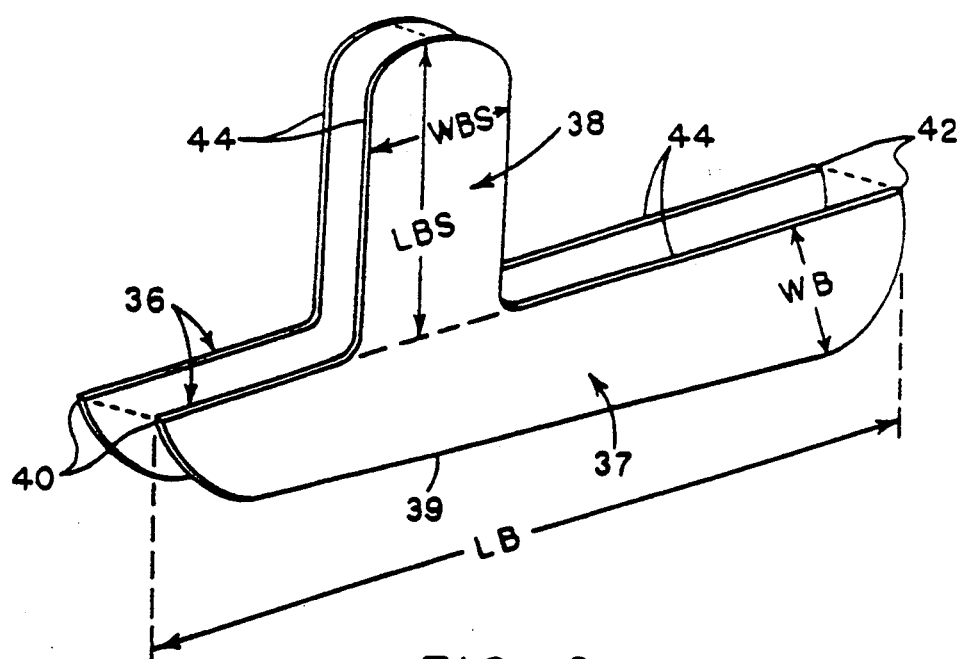
FIG. 6 is a pictorial depiction of the blanks of the baffle and sheath, prior to being joined.
Figure 7:
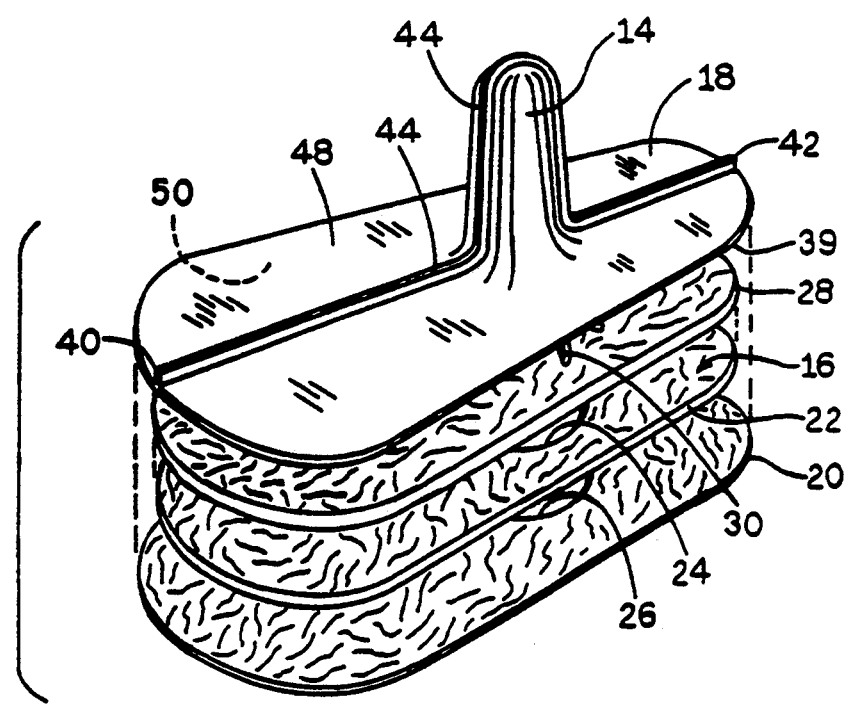
FIG. 7 is an exploded pictorial view showing the composite baffle layer and sheath, and the other layers of the external pad, prior to the assembly of the pad and the inversion of the sheath.

Referring to FIGS. 6 and 7, a method of forming the absorbent article 10 will be described. The absorbent layer 16, the cover 20 and the conducting layer 28 are made by cutting pieces, having appropriately the same size and shape, from sheets of the respective materials, in a conventional manner. The composite of baffle 18 and sheath 14 is readily fabricated from a film having the desired properties explained above. The desired result is that the material in the fabricated sheath 14 is substantially the same, including the same thickness as the material in fabricated baffle 18.

To fabricate the composite of baffle 18 and sheath 14, a pair of blanks 36 is cut from a sheet of film material. Each blank 36 includes a pad portion 37 and a sheath portion 38. Each blank 36 represents one half of the finished composite baffle 18 and sheath 14. The length of the pad portion 37, denoted (LB), of each blank 36 corresponds to a length, denoted (LP), of the finished external pad 12. The width of the external pad 12 portion of each blank 36, denoted (WB), at a given point along the length of the pad corresponds generally to half the width of the finished pad at the same point, denoted (WP). WB is slightly larger than one half of (WP) for bonding purposes described hereinafter. The length of the sheath portion 38 of the blank 36, denoted (LBS), corresponds generally to the length of the finished sheath 14, allowing for formation of the end of the sheath 14. The width of the sheath portion 38 of the blank 36, denoted (WBS), corresponds to slightly more than half of the circumference of the finished sheath 14.

The perimeter of each blank 36 comprises a perimeter edge portion 39 which extends from a first point 40 to a second point 42, along a path that describes what will be about half of the outer perimeter of the external pad 12. The perimeter further comprises a joinder edge portion 44 which extends from the first point 40 along the edge that encompasses the sheath portion 38 to the second point 42.

The composite of the baffle 18 and the sheath 14 is fabricated from the blanks 36, for example, by placing the pair of blanks 36 in a face-to-face relationship with each other, as suggested by the dashed lines in FIG. 6, and bonding the joinder edge portions 44 on the respective blanks 36 to each other thereby forming a bond line 46, see FIGS. 1 and 2. The preferred method of bonding is sonic or thermal welding. The resulting product is the composite of the baffle 18 and the sheath 14. The amount of material used to form the bond at the joinder edge portions 44 corresponds to the amount that the dimensions (WB) and (WBS) in the blanks 36 exceed half the corresponding dimensions in the external pad 12 and the sheath 14.

Referring to FIG. 7, after the blanks 36 are bonded, the pad portions 37 of the composite are disposed to form a single layer, having opposing sides 48 and 50. The sheath 14 is located on the side 48 of the layer. The bond line 46 traverses the surfaces of the baffle 18 where the blanks 36 are joined, and correspondingly traverses the sheath 14. The absorbent layer 16, the cover 20 and the conducting layer 28 are then bonded adjacent to the side 50 of the baffle 18 in the conventional manner of securing layers to each other to form a pad. This is opposite to the original positioning of the sheath 14. In the process, the openings 24, 26, and 30 are aligned as shown. The absorbent layer 16, the cover 20, and the conducting layer 28 secured to the baffle 18 form the external pad 12 portion of the feminine absorbent hygiene article 10. The sheath 14 is inverted through the openings 24, 26, and 30 to the side 50 of the baffle 18. In the process, the sheath 14 encounters the edges of the opening 30 whereby corresponding portions of the conducting layer 28 are disposed against the sheath 14 as shown, and interposed between the sheath 14 and the edges of the opening 24. The feminine absorbent hygiene article 10 is then ready for use in the manner described above.

It is preferred that no portion of the conducting layer 28 be disposed in the user's vagina. However, in some embodiments, the opening 30 can be constructed such that portions of the conducting layer 28 located adjacent to the opening 30 extend far enough along the length of the sheath 14 that some minor portions of the conducting layer 28 may extend slightly inside the introitus, whereby a small portion of the conducting layer 28 may be disposed inside the vagina. Such disposition is generally acceptable because only a small amount of material is so introduced into the vagina.

Those skilled in the art will now see that certain modifications can be made to the articles and methods herein disclosed with respect to the illustrated embodiments, without departing from the spirit of the instant invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

We claim:

1. A method of fabricating an absorbent feminine hygiene article, said feminine hygiene article comprising an external pad having a length, a width and a predetermined outer perimeter and shape, a soft flexible film baffle, and a soft flexible film sheath adapted to extend vertically from said external pad a distance sufficient to permit insertion of at least a portion of said sheath into a user's vagina when said external pad is placed against the user's labia majora, said method comprising the steps of:
    (a) selecting a soft and flexible film material suitable for contact with female genitalia, and impervious to body fluid;
    (b) cutting, from said film material, a pair of film blanks, each said blank being shaped such that, when said blanks are joined together, the combination thereof can comprise said predetermined outer perimeter and shape, each said blank comprising (i) a perimeter edge portion extending from a first point to a second point along a first perimeter path describing substantially half of said outer perimeter of said external pad, and (ii) a joinder edge portion adapted to be joined with the other said blank of said pair, said joinder edge portion extending between said first and second points along a second path, different from said first path, said second path, at an intermediate locus, extending away from said perimeter edge portion to thereby describe elements of said sheath;
    (c) joining said joinder edge portions of said blanks;
    (d) bending said joined blanks to create first and second generally parallel opposed major surfaces thereof, thereby creating a baffle corresponding to said predetermined outer perimeter and shape, said film sheath comprising an extension of said baffle on said second major surface and wherein said first major surface is disposed toward the user; and
    (e) joining an absorbent layer to said first major surface of said baffle to form said article.

2. The method of claim 1 wherein said absorbent layer has an opening adapted to receive said sheath therethrough, and edges, in combination, defining the perimeter of said opening, said method further comprising the step of extending said sheath through said opening in said absorbent layer.

3. The method of claim 2 further including positioning a conducting layer between said absorbent layer and said baffle, and extending said conducting layer to said sheath adjacent to and facing said absorbent layer, said conducting layer adapted to conduct body fluid therein in preference to releasing the body fluid to said absorbent layer.

4. The method of claim 3 further including placing a cover over said absorbent layer such that said absorbent layer is between said cover and said baffle, and including making openings in both said cover and said conducting layer, generally aligned with, and sized smaller than said opening in said absorbent layer, whereby said edges of said opening in said absorbent layer are spaced from said sheath by portions of said cover and said conducting layer.

5. The method of claim 4 wherein said cover, absorbent layer, and conducting layer are cut to approximately the same size and shape.

6. The method of claims 1 wherein said pair of blanks are cut from a film material having the same thickness as said baffle.

7. The method of claim 1 wherein said joinder edge portions of said blanks are placed in a face-to-face relationship with each other.

8. The method of claim 1 further including bonding said joinder edge portions of said blanks to form a bond line.

9. The method of claim 8 wherein said edge portions are sonic bonded.

10. The method of claim 8 wherein said edge portions are heat bonded.

11. The method of claim 4 wherein said absorbent article is fabricated by sequentially securing to said baffle said conducting layer, said absorbent layer, and said cover.

12. A method of fabricating an absorbent article, said article comprising a pad having a length, a width and a predetermined outer perimeter and shape, a soft flexible film baffle, and a soft flexible film sheath adapted to extend outwardly from said pad, said method comprising the steps of:
    (a) cutting a pair of film blanks, from a soft and flexible film material, each of said blanks being shaped such that, when said blanks are joined together, the combination thereof can comprise said predetermined outer perimeter and shape, each of said blanks comprising a perimeter edge portion describing substantially half of said outer perimeter of said external pad and a joinder edge portion adapted to be joined with the other said blank of said pair, said joinder edge portion extending away from said perimeter edge portion to thereby describe elements of said sheath;
    (b) joining said joinder edge portions of said blanks;
    (c) bending said joined blanks to create first and second generally parallel opposed major surfaces thereof, thereby creating a baffle corresponding to said predetermined outer perimeter and shape, said film sheath comprising an extension of said baffle on said second major surface; and (d) joining an absorbent layer to said first major surface of said baffle to form said article.

13. The method of claim 12 wherein said absorbent layer has an opening adapted to receive said sheath therethrough, and edges, in combination, defining the perimeter of said opening, said method further comprising the step of extending said sheath through said opening in said absorbent layer.

14. The method of claim 13 further including positioning a conducting layer between said absorbent layer and said baffle, and extending said conducting layer to said sheath adjacent to and facing said absorbent layer, said conducting layer adapted to conduct body fluid therein in preference to releasing the body fluid to said absorbent layer.

15. The method of claim 12 wherein said absorbent layer has an opening adapted to receive said sheath therethrough, and edges, in combination, defining the perimeter of said opening, said method further comprising the step of extending said sheath through said opening in said absorbent layer.

16. The method of claim 13 further including positioning a conducting layer between said absorbent layer and said baffle, and extending said conducting layer to said sheath adjacent to and facing said absorbent layer, said conducting layer adapted to conduct body fluid therein in preference to releasing the body fluid to said absorbent layer.

17. A method of manufacturing an absorbent feminine article having a cover, an absorbent and a baffle, wherein said baffle includes a flexible sheath adapted to extend outwardly from said baffle, said method comprising the steps of:

(a) cutting a pair of blanks from a material that is liquid-impermeable and acceptable for contacting a user's vagina, said blanks having a perimeter edge portion which defines about half of an outer perimeter of a pad portion and a joinder edge portion which includes a sheath portion;

(b) placing said pair of blanks in a face-to-face relationship and bonding said joinder edge portions on said blanks to each other thereby forming a bond line;

(c) spacing apart said pad portions to form a single layer having a first and second opposing sides, thereby creating a baffle and a sheath extending from said baffle on said second side; and (d) securing said absorbent layer to said first side to form said article.

* * * * *